(12) United States Patent
Chiang

(10) Patent No.: US 8,118,760 B2
(45) Date of Patent: Feb. 21, 2012

(54) JOINT BRACE AND A MOVEMENT RESTRAINING DEVICE THEREFOR

(75) Inventor: Pang-Ching Chiang, Taipei (TW)

(73) Assignee: Plus Meditech Co., Ltd, Tainan (TW)

( * ) Notice: Subject to any disclaimer, the term of this patent is extended or adjusted under 35 U.S.C. 154(b) by 73 days.

(21) Appl. No.: 12/829,581

(22) Filed: Jul. 2, 2010

(65) Prior Publication Data

US 2012/0004584 A1    Jan. 5, 2012

(51) Int. Cl.
*A61F 5/00* (2006.01)
(52) U.S. Cl. ............... 602/16; 602/23; 602/26
(58) Field of Classification Search ........... 602/16, 602/20, 21–28, 60–62; 128/869, 878–879, 128/882
See application file for complete search history.

(56) References Cited

U.S. PATENT DOCUMENTS

| | | | | | |
|---|---|---|---|---|---|
| 3,084,685 | A | * | 4/1963 | Lewis | 602/26 |
| 4,366,813 | A | * | 1/1983 | Nelson | 602/26 |
| 4,425,912 | A | * | 1/1984 | Harper | 602/26 |
| 5,261,871 | A | * | 11/1993 | Greenfield | 602/26 |
| 5,823,981 | A | * | 10/1998 | Grim et al. | 602/26 |

* cited by examiner

*Primary Examiner* — Michael A. Brown
(74) *Attorney, Agent, or Firm* — Davidson Berquist Jackson & Gowdey, LLP

(57) ABSTRACT

A movement restraining device for use in combination with an elastic wrap of a joint brace includes at least one elongated bendable member including a plurality of spaced-apart strips each of which has opposite strip surfaces parallel to the strip surfaces of the remaining ones of the strips, and first and second retaining plates facing each other. The strips further have first end portions substantially perpendicular to and fixed between the first and second retaining plates, and second end portions extending away from the first and second retaining plates.

10 Claims, 6 Drawing Sheets

JOINT BRACE AND A MOVEMENT RESTRAINING DEVICE THEREFOR

BACKGROUND OF THE INVENTION

1. Field of the Invention

This invention relates to a joint brace, more particularly to a movement restraining device for a joint brace to limit the range of angular motion of the joint, and a joint brace having said movement restraining device.

2. Description of the Related Art

Limb joints are an important part of the human body, and because of frequent movement, are easily injured. When a limb joint is injured, a brace is necessary to secure the joint to thereby prevent excess angular motion of the joint that may cause a second injury, especially to the joint ligament or muscle.

A frequently seen joint brace is a flexible tubular sleeve that is sleeved tightly on the limb joint so as to fix the joint. However, the effect of limiting the angular motion of the joint is poor with the use of such a conventional joint brace. Another kind of conventional joint brace includes a hinged plate assembly including two support plates connected pivotally to each other. Through the hinged plate assembly, the angular motion of the joint can be limited effectively. However, since the hinged plate assembly is large and heavy, the force to be exerted by the user to carry the brace around his or her limb joint is large.

SUMMARY OF THE INVENTION

Therefore, an object of the present invention is to provide a movement restraining device for a joint brace that is lightweight and that can limit the range of angular motion of the joint.

Another object of the present invention is to provide a joint brace having the aforesaid movement restraining device.

According to one aspect of this invention, a movement restraining device for use in combination with an elastic wrap of a joint brace comprises at least one elongated bendable member including a plurality of spaced-apart strips each of which has opposite strip surfaces parallel to the strip surfaces of the remaining ones of the strips, and first and second retaining plates facing each other. The strips further have first end portions substantially perpendicular to and fixed between the first and second retaining plates, and second end portions extending away from the first and second retaining plates.

According to another aspect of this invention, a joint brace comprises two movement restraining devices and an elastic wrap. Each movement restraining device includes two elongated bendable members. Each of the elongated bendable members includes a plurality of spaced-apart strips each of which has opposite strip surfaces parallel to the strip surfaces of the remaining ones of the strips, and first and second retaining plates facing each other. The strips further have first end portions substantially perpendicular to and fixed between the first and second retaining plates, and second end portions extending away from the first and second retaining plates. The strips of one of the bendable members are inserted between the strips of the other one of the bendable members in an alternating manner. The second end portions of one of the bendable members extend between the first and second retaining plates of the other one of the bendable members. The elastic wrap is adapted to wrap a limb joint, and has two elongated pockets for receiving respectively the movement restraining devices.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
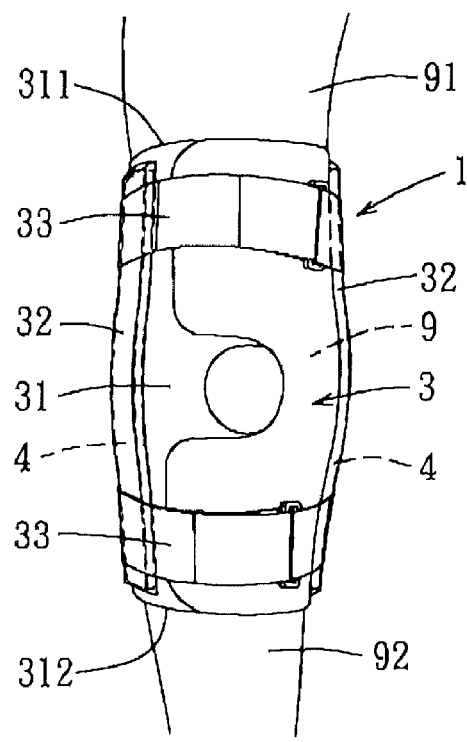
FIG. 1 is a schematic view of a joint brace according to the first preferred embodiment of the present invention in a state of use.

The above-mentioned and other technical contents, features, and effects of this invention will be clearly presented from the following detailed description of two preferred embodiments in coordination with the reference drawings.

Before this invention is described in detail, it should be noted that, in the following description, similar elements are designated by the same reference numerals.

Referring to FIGS. 1 to 7, a joint brace 1 according to the first preferred embodiment of the present invention comprises two movement restraining devices 4 and an elastic wrap 3.

Each of the movement restraining devices 4 includes two elongated bendable members 40. Each bendable member 40 has a retaining portion 41 and a plurality of spaced-apart strips 42. The retaining portion 41 includes first and second retaining plates 413, 414 (see FIG. 6) facing each other, a first end flange 415 projecting substantially perpendicularly from one lateral side of the second retaining plate 414, and a second end flange 412 projecting substantially perpendicularly from another lateral side of the second retaining plate 414. The first and second end flanges 415, 412 are interconnected at a corner of the second retaining plate 414 between said one lateral side and said another lateral side thereof.

Each strip 42 has opposite strip surfaces 424 parallel to the strip surfaces 424 of the remaining ones of the strips 42. That is, each two adjacent ones of the strips 42 are face-to-face with each other. The strips 42 further have first end portions 421 substantially perpendicular to and fixed between the first and second retaining plates 413, 414, and second end portions 422 extending away from the first and second retaining plates 413, 414. The first end portions 421 of the strips 42 have terminal ends fixed to the first end flange 415, and are parallel to the second end flange 412. Each strip 42 further has an intermediate portion 423 that is between the first and second end portions 421, 422 and that has two opposite strip edge faces 425 connected between the opposite strip surfaces 424. In this embodiment, the second retaining plate 414 is flat, and is flush with one of the strip edge faces 425 of the strips 42. That is, the side of the bendable member 40 having the second retaining plate 414 is used for abutting against a limb joint 9 (see FIG. 1) of a user. Further, the second end portion 422 of each strip 42 has a width smaller than that of the intermediate portion 423, so that the second end portion 422 of each strip 42 can be received within the retaining portion 41 of the other bendable member 40, and so that each of the strips 42 is stepped. The first retaining plate 413, in this embodiment, is bulging. However, in an alternative embodiment, the first retaining plate 413 may be made flat.

Figure 2:
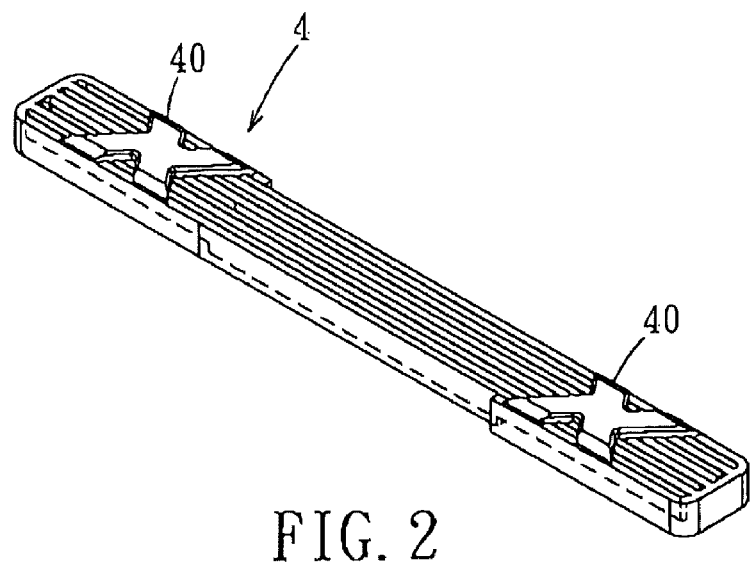
FIG. 2 is a perspective view of a movement restraining device of the first preferred embodiment.
Figure 3:
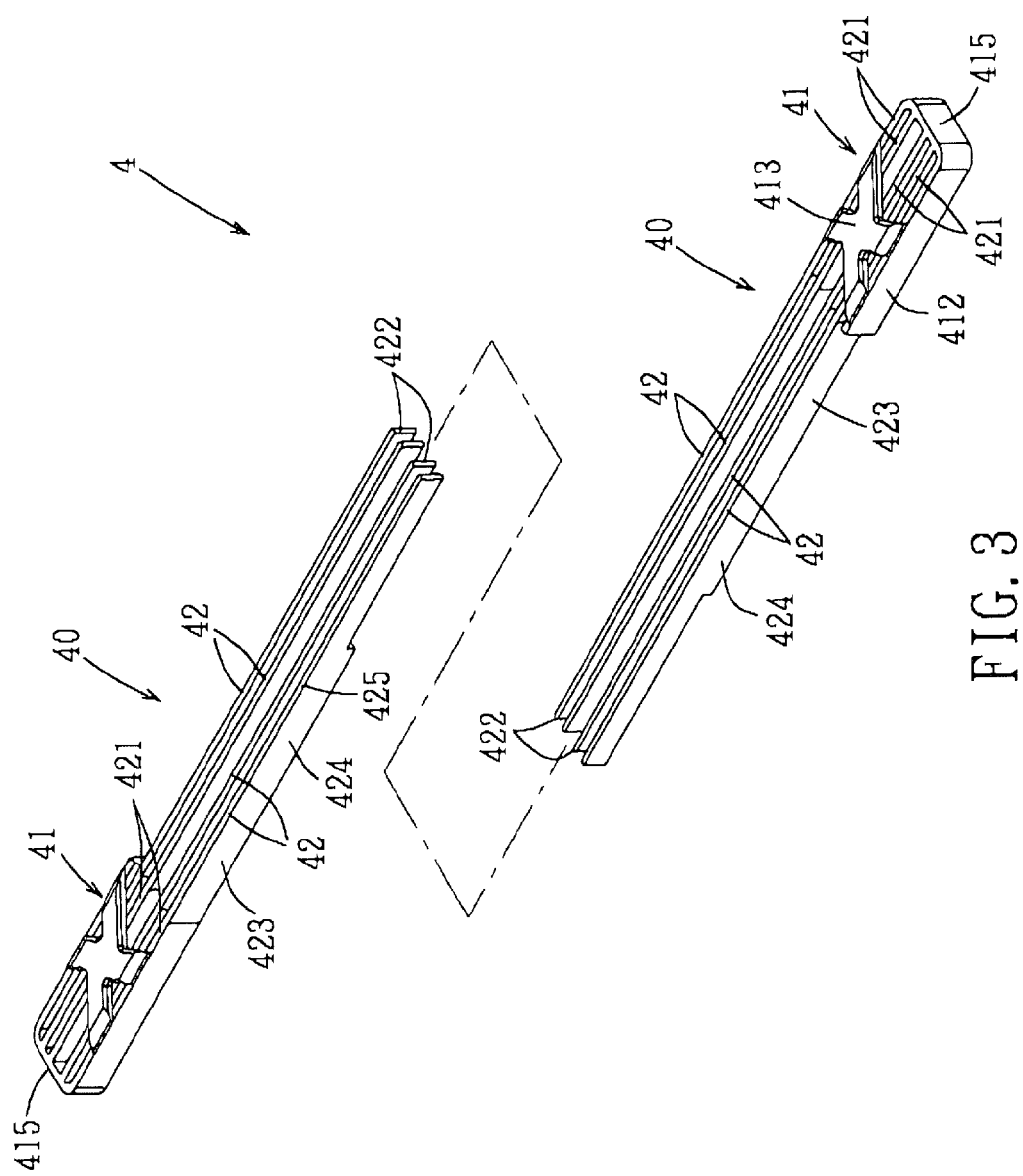
FIG. 3 is an exploded perspective view of the movement restraining device of the first preferred embodiment.
Figure 4:
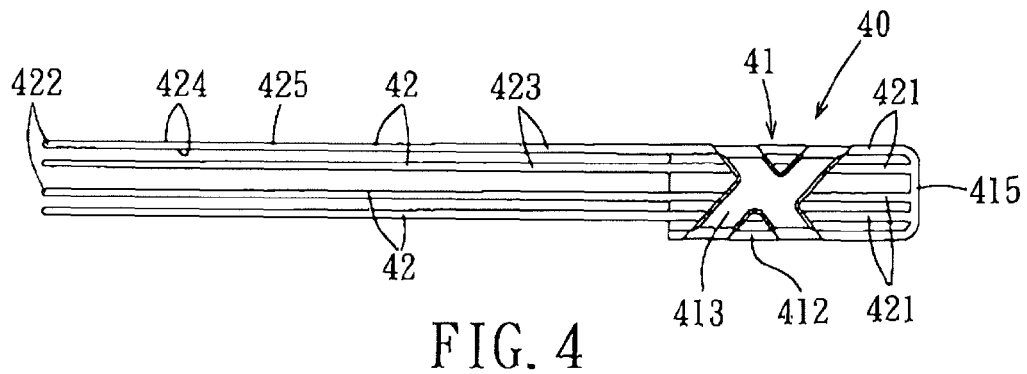
FIG. 4 is a schematic top view of a bendable member of the movement restraining device.
Figure 5:
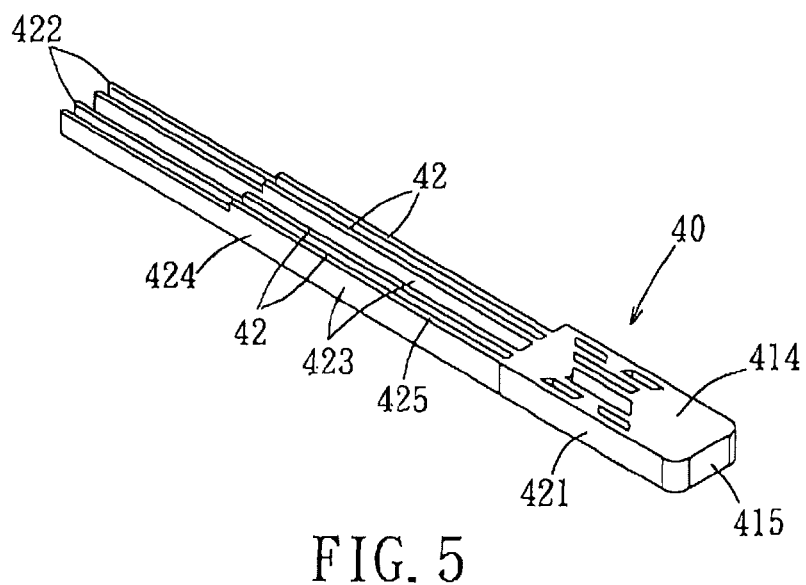
FIG. 5 is a perspective view of the bendable member of the movement restraining device.
Figure 6:
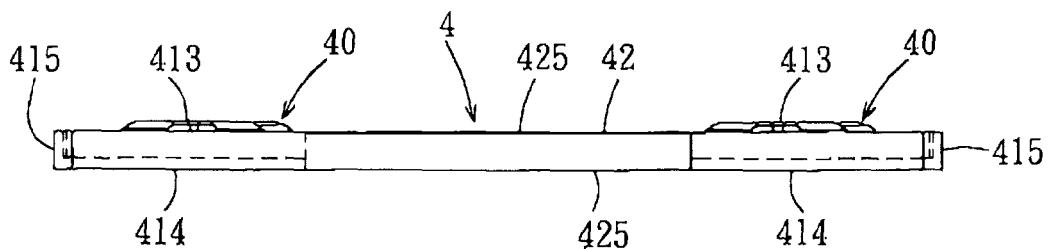
FIG. 6 is a schematic side view of the movement restraining device.
Figure 7:
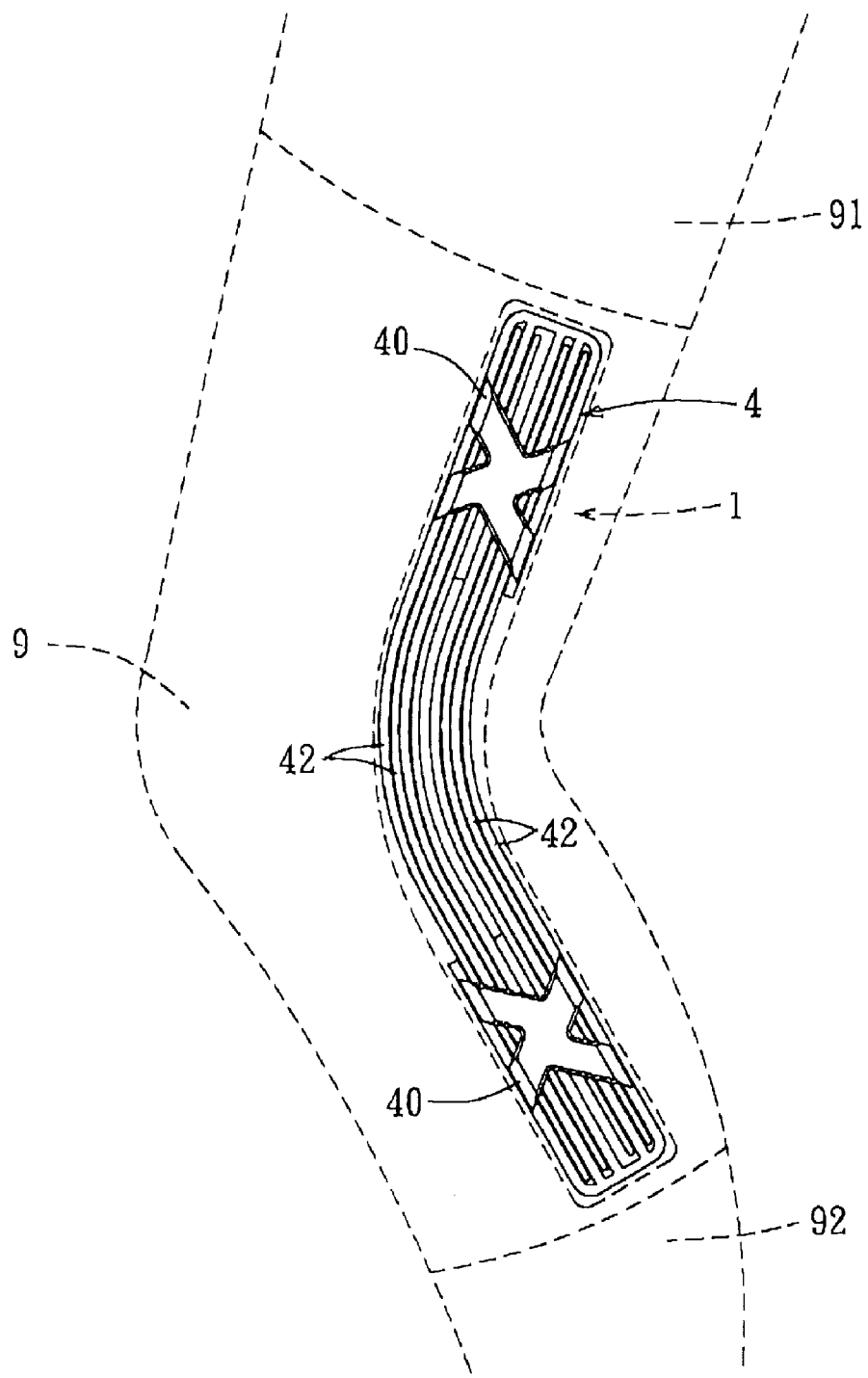
FIG. 7 illustrates how the movement restraining device bends when a limb joint flexes.

With reference to FIGS. 2, 3, and 6, the strips 42 of one of the bendable members 40 are inserted between the strips 42 of the other bendable member 4 in an alternating manner with the second end portions 422 thereof extending between the first and second retaining plates 413, 414 of the other bendable member 40 and limited thereto. That is, the second end portions 422 of the strips 42 of one of the bendable members 40 are inserted within the retaining portion 41 of the other bendable member 40, and are limited within a space defined by the first and second retaining plates 413, 414 and the first and second end flanges 415, 412. Further, since the strips 42 of one of the bendable members 40 are arranged alternately with the strips 42 of the other bendable member 40, a gap still exists between each two adjacent ones of the strips 42. With reference to FIG. 7, the movement restraining device 4 is bendable at the intermediate portions 423 of the strips 42. The intermediate portions 423 of the strips 42 are bendable about axes parallel to the strip surfaces 424 (see FIG. 3) thereof, and are not bendable about axes parallel to the strip edge faces 425 (see FIG. 3) of the strips 42. Therefore, when the joint brace 1 is wrapped around the user's joint, the intermediate portions 423 of the strips 42 of the movement restraining devices 4 can bend forward, but not leftward and rightward.

Moreover, the two bendable members 40 can be made of plastic materials having different coefficients of elasticity. That is, the bendable members 40 can have different degrees of hardness and softness. Through the combination of the bendable members 40, the hardness and softness (resiliency) of the movement restraining device 4 can be adjusted to conform to the different rehabilitation stages required by the same or different users. Examples of suitable plastic materials include nylon, polypropylene (PP), thermoplastic rubber (TPR), thermoplastic elastomer (TPE), and polyoxymethylene (POM).

With reference to FIGS. 1, 6, and 7, the elastic wrap 3 is adapted to be wrapped around a limb joint 9, and includes a main body 31, and two elongated pockets 32 provided on the main body 3 for receiving respectively the movement restraining devices 4. The main body 31 has upper and lower sides 311, 312 located respectively on two body portions 91, 92 interconnected by the limb joint 9 when the elastic wrap 3 is wrapped around the limb joint 9. The elastic wrap 3 further includes two fastening straps 33 provided on the main body 31 in proximity to the upper and lower sides 311, 312, respectively. The fastening straps 33 extend around the main body 31 in proximity respectively to the upper and lower sides 311, 312 thereof, and extend transversely over the pockets 32, thereby fixing the movement restraining devices 4 to the body portions 91, 92 and limiting movement thereof. The side of each movement restraining device 4 having the second retaining plate 414 faces the limb joint 9. Through the unidirectional bendability of the movement restraining devices 4, the limb joint 9 can be prevented from twisting, and through the adjustable elasticity of the movement restraining devices 4, the range of angular motion of the limb joint 9 can be limited, thereby achieving the purpose of protecting the limb joint 9. Further, each movement restraining device 4 has a simple structure, and is lightweight, so that the joint brace 1 can be worn comfortably without the user having to expend a great deal of energy to carry the joint brace 1. In this embodiment, a knee joint is exemplified. However, the joint brace 1 of the present invention may also be worn around an ankle joint or an elbow joint.

Figure 8:
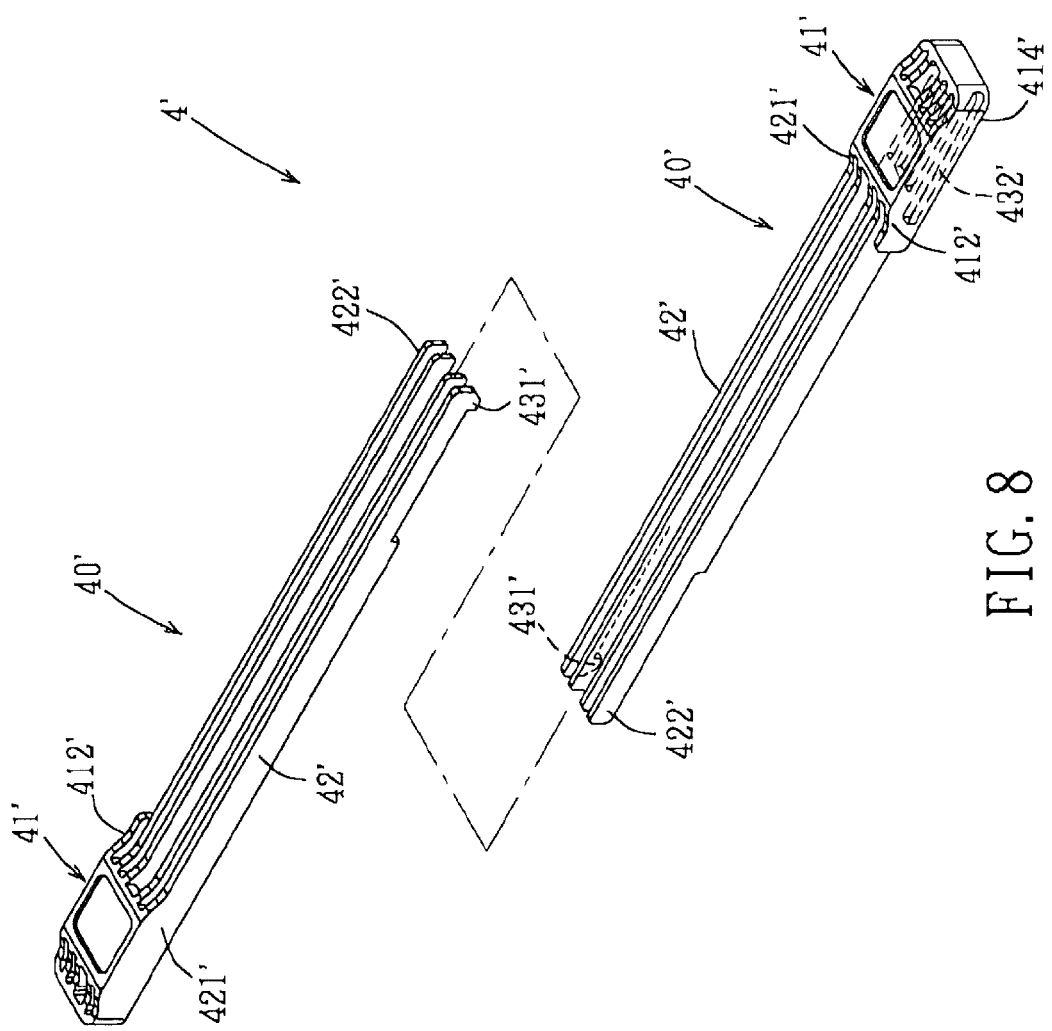
FIG. 8 is an exploded perspective view of a movement restraining device of a joint brace according to the second preferred embodiment of the present invention.
Figure 9:
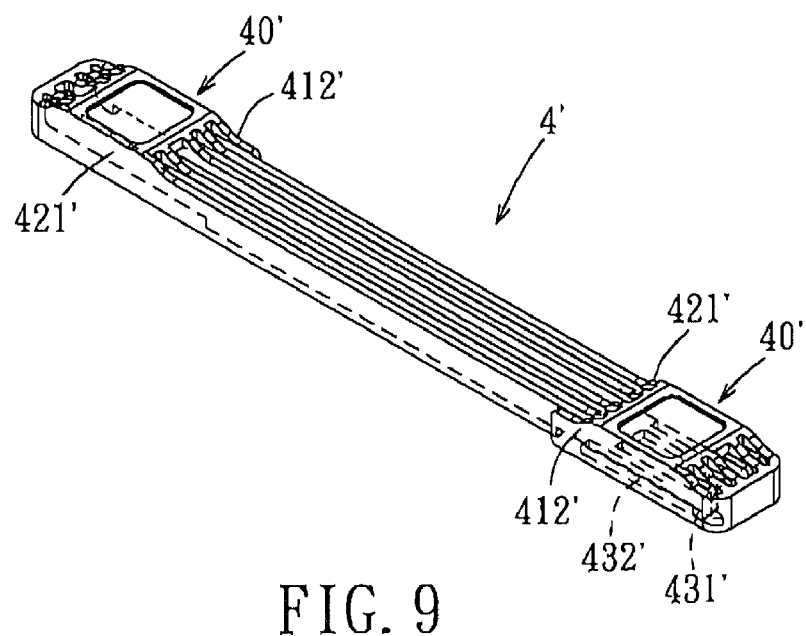
FIG. 9 is a perspective view of the movement restraining device of the second preferred embodiment in an assembled state.
Figure 10:
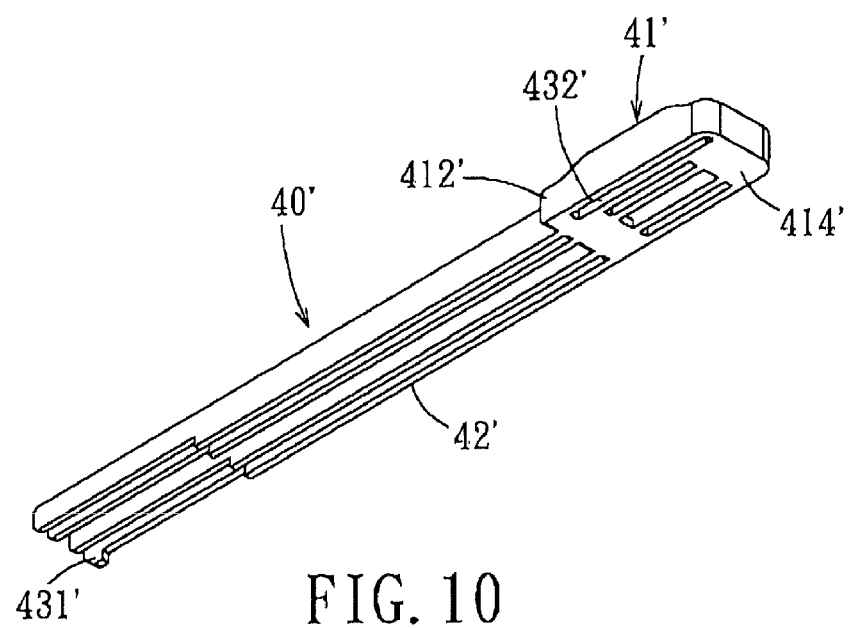
FIG. 10 is a perspective view of a bendable member of the movement restraining device of the second preferred embodiment.

FIGS. 8 to 10 illustrate a movement restraining device 4' of a joint brace 1 according to the second preferred embodiment of the present invention. The movement restraining device 4' is similar to that described in the first preferred embodiment. However, in this embodiment, each of the bendable members 40' of the movement restraining device 4' further includes a limiting unit to limit separation of the bendable members 40'. The limiting unit includes a hook 431' provided on a free end of the second end portion 422' of the strip 42' that is disposed farthest from the second end flange 412', and an elongated slot 432' formed in the second retaining plate 414' in proximity to the second end flange 412'. The hook 431' of each bendable member 40' extends slidably into the slot 432' of the other bendable member 40'. Through such a connection, when the extent of bending of the movement restraining device 4' is large, the displacement of the strip 42', which is farthest from the second end flange 412' of one of the bendable members 40', can be limited to prevent removal of the strip 42 from the retaining portion 41' of the other bendable member 40'. That is, removal of the strip 42 which is farthest from the second end flange 412' of one of the bendable members 40' from the blocking range of the second end flange 412' of the other bendable member 40' can be prevented.

From the aforesaid description, each of the movement restraining devices 4, 4' of the joint brace 1 of the present invention has a unidirectional and adjustable degree of bendability to limit the range of angular motion of the limb joint 9 to thereby conform to different use requirements. Further, the movement restraining devices 4, 4' have simple structures, and are lightweight, so that the joint brace 1 can be worn comfortably by the user without the user having to expend a great deal of energy to carry the joint brace 1. Therefore, the objects of the present invention can be realized.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

I claim:

1. A movement restraining device for use in combination with an elastic wrap of a joint brace, comprising:
   at least one elongated bendable member including a plurality of spaced-apart strips each of which has opposite strip surfaces parallel to said strip surfaces of the remaining ones of said strips, and first and second retaining plates facing each other, said strips further having first end portions substantially perpendicular to and fixed between said first and second retaining plates, and second end portions extending away from said first and second retaining plates.

2. The movement restraining device of claim 1, which comprises a pair of said bendable members, wherein said strips of one of said bendable members are inserted between said strips of the other one of said bendable members in an alternating manner, and said second end portions of one of said bendable members extend between said first and second retaining plates of the other one of said bendable members.

3. The movement restraining device of claim 2, wherein each of said bendable members further includes a first, end flange projecting substantially perpendicularly from one lateral side of said second retaining plate and fixed to a terminal end of each of said first end portions of said strips, and a second end flange projecting substantially perpendicularly from another lateral side of said second retaining plate and parallel to said first end portions of said strips, said first and second end flanges being interconnected at a corner of said second retaining plate between said one lateral side and said another lateral side.

4. The movement restraining device of claim 3, wherein each of said strips further has an intermediate portion that is between said first and second end portions and that has two opposite strip edge faces connected between said opposite strip surfaces, said second retaining plate being flat, and being flush with one of said strip edge faces of said strips.

5. The movement restraining device of claim 4, wherein each of said strips has said second end portion thereof with a width smaller than that of said intermediate portion thereof.

6. The movement restraining device of claim 2, wherein each of said bendable members further has a limiting unit disposed on said second end portion of one of said strips and on said second retaining plate to limit separation of said bendable members.

7. The movement restraining device of claim 6, wherein each of said bendable members has a slot formed in said second retaining plate proximate to said second end flange, and a hook formed on a free end of said second end portion of one of said strips that is farthest from said second end flange, said hook of each of said bendable members extending into said slot of the other one of said bendable members, said limiting unit being configured to include said slot and said hook.

8. The movement restraining device of claim 2, wherein said two bendable members have different coefficients of elasticity.

9. A joint brace comprising:
two movement restraining devices each including
two elongated bendable members;
each of said bendable members including a plurality of spaced-apart strips each of which has opposite strip surfaces parallel to said strip surfaces of the remaining ones of said strips, and first and second retaining plates facing each other, said strips further having first end portions substantially perpendicular to and fixed between said first and second retaining plates, and second end portions extending away from said first and second retaining plates;
wherein said strips of one of said bendable members are inserted between said strips of the other one of said bendable members in an alternating manner, and said second end portions of one of said bendable members extend between said first and second retaining plates of the other one of said bendable members; and
an elastic wrap adapted to wrap a limb joint and having two elongated pockets for receiving respectively said movement restraining devices.

10. The joint brace of claim 9, further comprising two fastening straps to extend around said elastic wrap, wherein, when said fastening straps extend around said elastic wrap, said fastening straps extend transversely over said pockets and limit movement of said movement restraining devices.

* * * * *